United States Patent
Kayama et al.

(10) Patent No.: US 10,234,420 B2
(45) Date of Patent: Mar. 19, 2019

(54) GAS SENSOR CONTROL DEVICE

(71) Applicant: DENSO CORPORATION, Kariya, Aichi-pref. (JP)

(72) Inventors: Ryozo Kayama, Kariya (JP); Yukihiro Yamashita, Kariya (JP); Yoshihiro Sakashita, Kariya (JP)

(73) Assignee: DENSO CORPORATION, Kariya (JP)

( * ) Notice: Subject to any disclaimer, the term of this patent is extended or adjusted under 35 U.S.C. 154(b) by 134 days.

(21) Appl. No.: 14/917,326

(22) PCT Filed: Sep. 11, 2014

(86) PCT No.: PCT/JP2014/004717
§ 371 (c)(1),
(2) Date: Mar. 8, 2016

(87) PCT Pub. No.: WO2015/040843
PCT Pub. Date: Mar. 26, 2015

(65) Prior Publication Data
US 2016/0223488 A1    Aug. 4, 2016

(30) Foreign Application Priority Data

Sep. 20, 2013  (JP) ................................. 2013-196062
Nov. 29, 2013  (JP) ................................. 2013-246947

(51) Int. Cl.
| *G01N 27/419* | (2006.01) |
| *G01N 27/417* | (2006.01) |
| *F01N 11/00*  | (2006.01) |
(Continued)

(52) U.S. Cl.
CPC ......... *G01N 27/419* (2013.01); *F01N 11/007* (2013.01); *G01N 27/409* (2013.01);
(Continued)

(58) Field of Classification Search
CPC .... G01N 27/419; G01N 27/409; G01N 27/41; G01N 27/4175; F01N 11/007; Y02T 10/47
See application file for complete search history.

(56) References Cited

U.S. PATENT DOCUMENTS

| 2004/0000479 A1* | 1/2004 | Katafuchi ............ G01N 27/419 204/424 |
| 2004/0050695 A1  | 3/2004 | Haraguchi et al. |

(Continued)

FOREIGN PATENT DOCUMENTS

| JP | 2006-267126 | 10/2006 |
| JP | 2006-267127 | 10/2006 |

(Continued)

OTHER PUBLICATIONS

International Search Report for PCT/JP2014/004717 dated Dec. 16, 2014, 4 pages.

(Continued)

*Primary Examiner* — J. Christopher Ball
(74) *Attorney, Agent, or Firm* — Nixon & Vanderhye P.C.

(57) ABSTRACT

A NOx sensor includes a pump cell, a monitor cell, and a sensor cell, and the pump cell discharges an oxygen in an exhaust gas introduced into a chamber. The sensor cell outputs a detected signal depending on a concentration of a NOx according to a gas after the oxygen is discharged. A microcomputer of a sensor control circuit temporarily changes an amount of the oxygen discharged by the pump cell, and then calculates output change amounts ΔIp, ΔIs, and ΔIm of the cells. The microcomputer performs a correction of the concentration of the NOx detected by the sensor cell and a deterioration diagnosis of the sensor cell, based on the output change amounts ΔIp, ΔIs, and ΔIm of the cells. When the sensor cell current Is is smaller than the (Continued)

monitor cell current Im, the microcomputer determines that the NOx sensor has an abnormality.

11 Claims, 10 Drawing Sheets

(51) Int. Cl.
*G01N 27/409* (2006.01)
*G01N 27/41* (2006.01)

(52) U.S. Cl.
CPC ......... *G01N 27/41* (2013.01); *G01N 27/4175* (2013.01); *Y02T 10/47* (2013.01)

(56) References Cited

U.S. PATENT DOCUMENTS

2009/0205957 A1* 8/2009 Hada .................. G01N 27/4065
   204/406

2009/0242427 A1 10/2009 Muroguchi et al.

FOREIGN PATENT DOCUMENTS

| | | |
|---|---|---|
| JP | 2007-147386 | 6/2007 |
| JP | 2007-278732 | 10/2007 |
| JP | 2008-275561 | 11/2008 |
| JP | 2009-175013 | 8/2009 |
| JP | 2009-175014 | 8/2009 |
| JP | 2009-192289 | 8/2009 |
| JP | 2009-257888 | 11/2009 |

OTHER PUBLICATIONS

Written Opinion of the ISA for PCT/JP2014/004717 dated Dec. 16, 2014, 15 pages.

* cited by examiner

FIG. 11
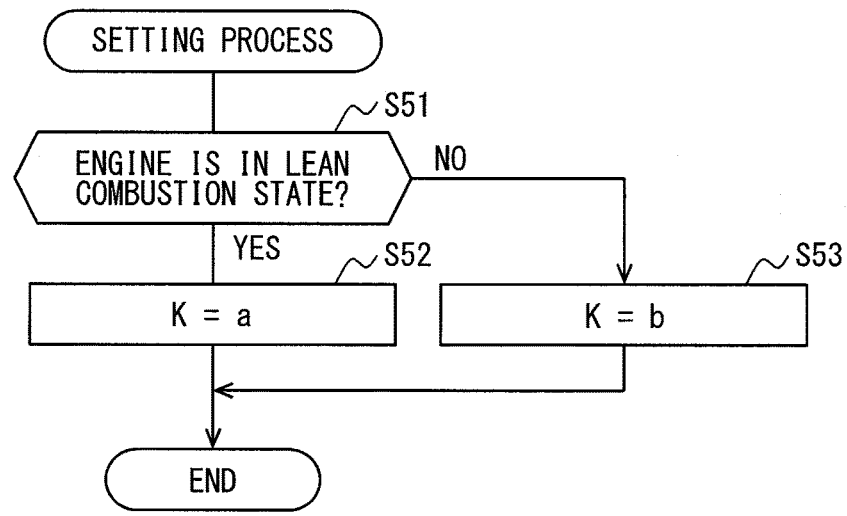
(a)
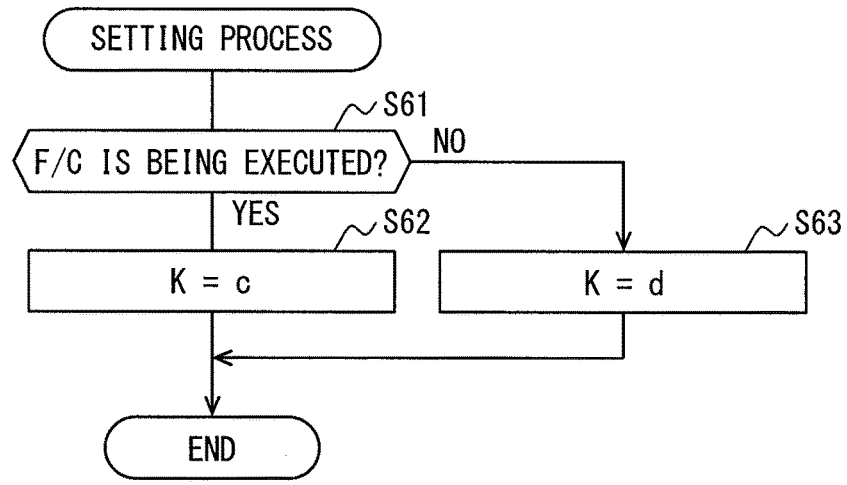
(b)

GAS SENSOR CONTROL DEVICE

CROSS REFERENCE TO RELATED APPLICATION

This application is the U.S. national phase of International Application No. PCT/JP2014/004717 filed Sep. 11, 2014 which designated the U.S. and claims priority to Japanese Patent Application No. 2013-196062 filed on Sep. 20, 2013 and Japanese Patent Application No. 2013-246947 filed on Nov. 29, 2013, the entire contents of each of which are incorporated herein by reference.

TECHNICAL FIELD

This disclosure relates to a gas sensor control device.

BACKGROUND ART

Patent Literature 1 discloses a gas sensor which takes an exhaust gas discharged from an on-vehicle engine as an object of a detection and detects a NOx concentration of the exhaust gas. The gas sensor (NOx sensor) includes a pump cell, a monitor cell, and a sensor cell each having a solid electrolytic element and a pair of electrodes disposed on the solid electrolytic element and uses the pump cell to discharge an oxygen in the exhaust gas introduced into a chamber and uses the sensor cell to detect the NOx concentration of the exhaust gas after the oxygen has been discharged. A deterioration diagnosing apparatus which diagnoses a deterioration of the gas sensor forcibly changes an applied voltage that is applied to the pump cell and diagnoses the deterioration of the gas sensor based on a change of an output of the sensor cell caused by a switching of the applied voltage. In the deterioration diagnosing apparatus, the output of the sensor cell is corrected based on an amount of a change of the applied voltage and an amount of the change of the output of the sensor cell.

Patent Literature 2 discloses various techniques to perform an abnormality diagnosis of the gas sensor of the above kind. For example, in the techniques disclosed in Patent Literature 2, a deterioration detection cell is provided in the vicinity of a sensor cell and an output corresponding to an output of a deterioration product of the sensor cell is obtained by the deterioration detection cell. It is determined whether or not a NOx sensor has deteriorated by comparing an output of the sensor cell with the output of the deterioration detection cell.

In Patent Literature 1, however, even when a constant voltage is applied to the pump cell, an amperage of a current flowing through the pump cell may be an amperage that is undesired. Further, it is possible that an accuracy of a deterioration diagnosis of the sensor cell may be decreased or an output correction of the sensor cell may be improperly performed. For example, in the pump cell, a pump cell current that is the current flowing through the pump cell (i.e., an amount of the oxygen discharged by the pump cell) is changed depending on the deterioration or an activation state, so as to affect a residual oxygen concentration that is a concentration of the oxygen that is residual in the chamber. The output of the sensor cell is changed by an effect applied to the residual oxygen concentration, with a result that the deterioration diagnosis or the output correction may be improperly performed.

In Patent Literature 2, since it is necessary to provide the deterioration detection cell other than the pump cell, the monitor cell, and the sensor cell to detect a sensor deterioration, a structure becomes complicated.

PRIOR ART LITERATURES

Patent Literature

Patent Literature 1: JP2009-175013A
Patent Literature 2: JP2009-175014A

SUMMARY OF INVENTION

It is an object of the present disclosure to provide a gas sensor control device which properly controls a gas sensor and can properly diagnose an abnormality of the gas sensor without complicating a structure.

According to a first aspect of the present disclosure, a gas sensor control device is applied to a gas sensor including a first cell and a second cell each having a solid electrolytic element and a pair of electrodes disposed on the solid electrolytic element. The gas sensor discharging an oxygen in a detected gas introduced into a gas chamber, by using the first cell, and the gas sensor detecting a concentration of a specific component from a gas after the oxygen is discharged, by using the second cell. The gas sensor control device includes an oxygen discharge amount changing section temporarily changing an oxygen discharge amount that is an amount of the oxygen that is discharged, by the first cell, a first calculating section calculating an actual discharge amount that is an actual amount of a change of the oxygen discharged when the oxygen discharge amount is changed by the oxygen discharge amount changing section, a second calculating section calculating an amount of output change which occurs in the second cell as a result of changing the oxygen discharge amount by the oxygen discharge amount changing section, and a main control section performing at least either correction of the concentration of the specific component as detected by the second cell or deterioration diagnosis of the second cell, based on the actual discharge amount as calculated by the first calculating section and the amount of output change of the second cell as calculated by the second calculating section.

When the amount of the oxygen discharged by the first cell (pump cell) is changed, the actual discharge amount (actual amount of the change of the oxygen that is discharged) caused by the change is calculated and at the same time an output change amount of the second cell (sensor cell) is calculated. In this case, even though an actual amount (oxygen pumping amount) of the oxygen that is discharged relative to an instruction of an oxygen discharge is changed in response to a deterioration state or an active state in the first cell, the actual amount of the oxygen that is discharged can be monitored. Since a correction of a concentration of a specific component that is detected by the second cell and a deterioration diagnosis of the second cell are performed, an accuracy in a calculation of the concentration and the deterioration diagnosis can be improved. As a consequence, the gas sensor can be controlled properly.

According to a second aspect of the present disclosure, the gas sensor control device is applied to a gas sensor including a pump cell, a monitor cell, and a sensor cell each having a solid electrolytic element and a pair of electrodes disposed on the solid electrolytic element in which in the gas sensor. The pump cell discharges oxygen in a gas to be detected, introduced into a gas chamber, and after discharging the oxygen, the monitor cell outputs a signal depending on a residual oxygen concentration in the gas chamber, and the sensor cell outputs a signal depending on a concentration of a specific component other than oxygen in the gas chamber. The device includes an acquiring section acquiring a monitor cell detected value calculated based on the output signal of the monitor cell and a sensor cell detected value calculated based on the output signal of the sensor cell, and an abnormality diagnosing section determining that the gas sensor has an abnormality when the sensor cell detected value is smaller than the monitor cell detected value.

The gas sensor is a NOx sensor detecting a concentration of a NOx in the exhaust gas discharged from the engine, and includes the pump cell, the monitor cell, and the sensor cell. The gas sensor detects the residual oxygen concentration in the gas chamber by the monitor cell from the gas after the oxygen is discharged by the pump cell, and detects a concentration of a specific component other than the oxygen by the sensor cell. In this case, a detected output is obtained by the monitor cell according to an amount of the residual oxygen, and a detected output is obtained by the sensor cell according to an amount of the residual oxygen and an amount of the specific component other than the oxygen. In the NOx sensor, the sensor cell detected value should be larger than the monitor cell detected value. When the sensor cell detected value is smaller than the monitor cell detected value, the NOx sensor can be determined to have an abnormality. In such an abnormality diagnosis, a configuration of the NOx sensor does not need to be altered. Thus, the abnormality diagnosis of the NOx sensor can be performed without complicating the configuration.

BRIEF DESCRIPTION OF DRAWINGS

The above and other objects, features and advantages of the present disclosure will become more apparent from the following detailed description made with reference to the accompanying drawings. In the drawings:

FIG. 11 is a flowchart showing a setting process setting a criterial value.

DESCRIPTION OF EMBODIMENTS

Next, an embodiment of a gas sensor control device according to the present disclosure will be described referring to drawings. According to the embodiment, a NOx concentration detector uses a NOx sensor provided in an exhaust pipe of an on-vehicle engine (internal combustion engine) to detect a NOx concentration of an exhaust gas based on an output of the NOx sensor. The engine system to which the NOx concentration detector is applied is assumed to have a structure as shown in FIG. 2.

Figure 2:
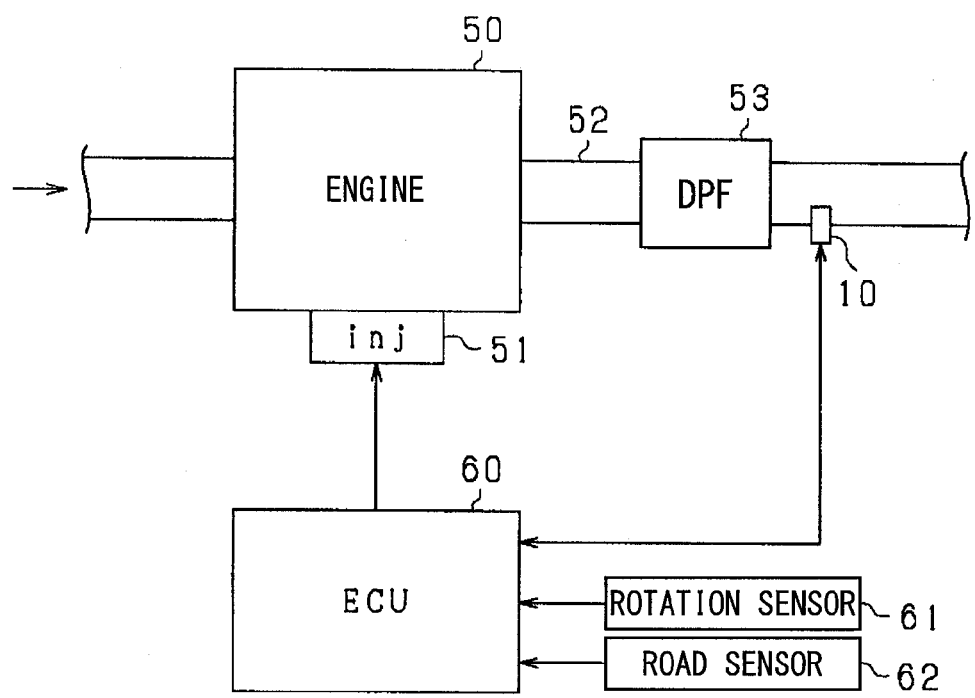
FIG. 2 is a block diagram showing an outline of an engine system.

As shown in FIG. 2, an engine 50 is, for example, a multi-cylinder diesel engine, and includes plural injectors (inj) 51 which inject a fuel. An exhaust pipe 52 of the engine 50 is provided with an exhaust gas purifier (DPF) 53. The exhaust gas purifier 53 is, for example, a NOx purifying catalyst such as a NOx occlusion reduction catalyst or an ammonia selection reduction catalyst. When the exhaust gas passes through the exhaust gas purifier 53, a NOx is purified. A NOx sensor 10 detecting a NOx concentration of the exhaust gas is located at a position downstream of the exhaust gas purifier 53. As show in FIG. 2, the NOx sensor 10 is located at a position downstream of the exhaust gas purifier 53. However, the NOx sensor 10 may be located at a position upstream of the exhaust gas purifier 53, or NOx sensors 10 may be located at position upstream and downstream of the exhaust gas purifier 53.

An ECU 60 is an electronic control unit which has a known microcomputer including a CPU and various memories. The ECU 60 receives not only a detection signal from the NOx sensor 10 but also detection signals from a rotation sensor 61 detecting a rotation speed of the engine 50 and a load sensor 62 detecting an engine load such as an accelerator opening degree. The ECU 60 performs a fuel injection control of the injectors 51 and a deterioration diagnosis of the exhaust gas purifier 53 based on the detection signals.

Figure 1:
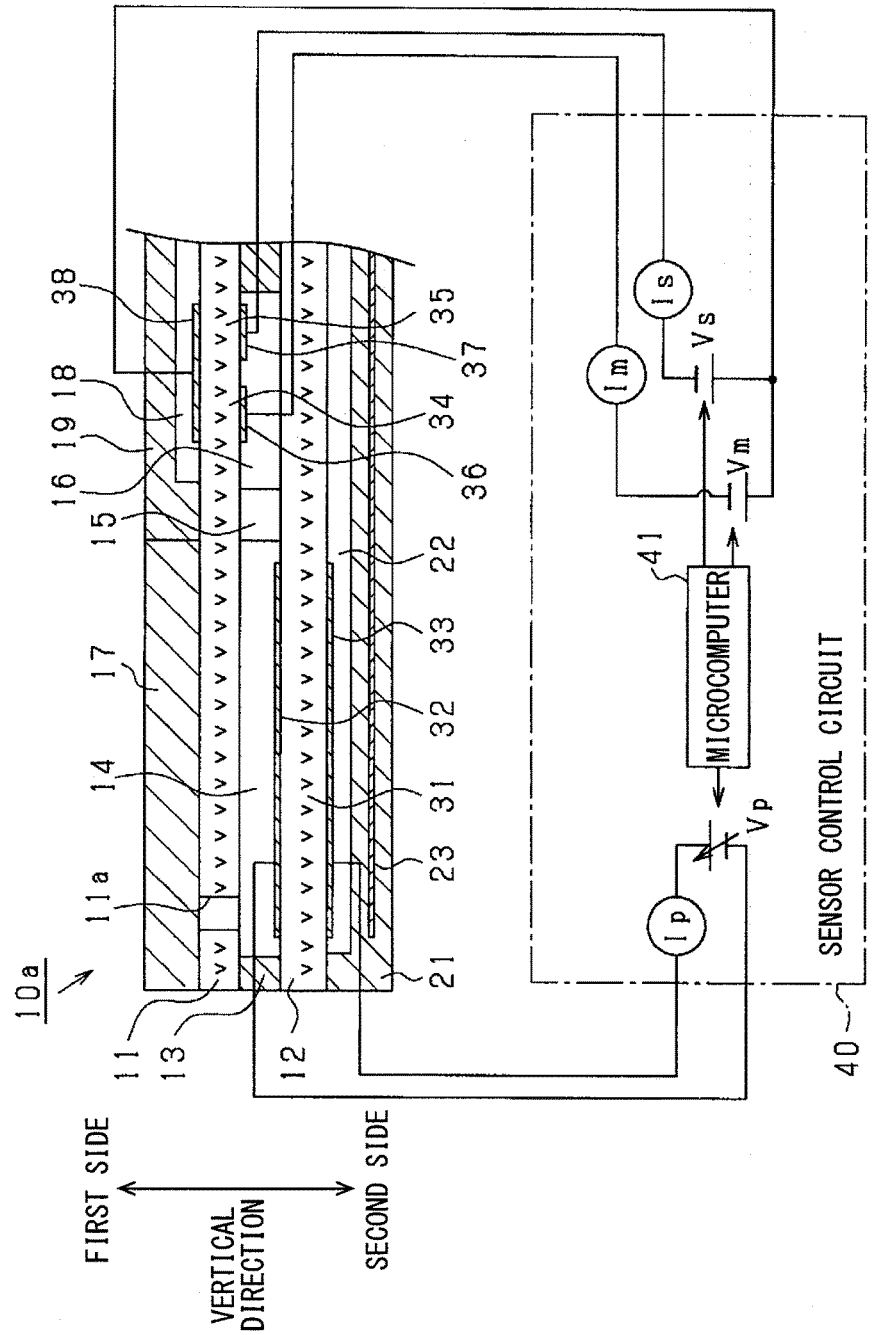
FIG. 1 is a block diagram showing an internal structure of an element of a NOx sensor and a sensor control circuit.

Next, a sensor element 10a which constitutes the NOx sensor 10 will be described referring to FIG. 1. The sensor element 10a has a laminated structure and an internal structure of the sensor element 10a is shown in FIG. 1. A base end of the sensor element 10a in a longitudinal direction is a part to which the exhaust pipe 52 is attached, and a front end of the sensor element 10a in the longitudinal direction extends toward the exhaust pipe 52. The sensor element 10a has a three-cell structure including a pump cell, a sensor cell, and a monitor cell, in which the cells are laminated. Since the monitor cell has a function discharging the oxygen in the gas which is similar to the pump cell, the monitor cell may be called as an auxiliary pump cell or a second pump cell.

In the sensor element 10a, solid electrolytic elements 11 and 12, which are made of an oxygen ion conductive material such as zirconia and are sheet shaped, are laminated vertically with a predetermined interval between them through a spacer 13 made of an insulating material such as an alumina. The solid electrolytic element 11, which is located on a first side in a vertical direction relative to the solid electrolytic element 12, has an exhaust-gas introduction port 11a, and the exhaust gas around the sensor element 10a is introduced into a first chamber 14 through the exhaust-gas introduction port 11a. The first chamber 14 communicates with a second chamber 16 through a throttling part 15. Both the chambers 14 and 16 are equivalent to gas chambers. A porous diffusion layer 17 which controls the exhaust gas to flow in and out with a prescribed diffusion resistance and an insulating layer 19 which forms an air path 18 are provided on the first side of the solid electrolytic element 11 in the vertical direction. In other words, the solid electrolytic element 11 is disposed between the solid electrolytic element 12, the porous diffusion layer 17, and insulating layer 19.

An insulating layer 21 made of an alumina or the like is provided on a second side of the solid electrolytic element 12 in the vertical direction, and an air path 22 is formed by the insulating layer 21. A heater 23 which heats the entire sensor is laid in the insulating layer 21. In this case, a pump cell 31, a monitor cell 34, and a sensor cell 35 are heated by the heater 23 to improve an activation of the cells 31, 34, and 35. The heater 23 is a heating element which generates thermal energy when an electric power is supplied from a battery power source that is not shown.

In the solid electrolytic element 12, which is located on the second side in the vertical direction, relative to the solid electrolytic element 11, has the pump cell 31 facing the first chamber 14, and the pump cell 31 suctions and discharges the oxygen in the exhaust gas introduced into the first chamber 14 to adjust a residual oxygen concentration in the first chamber 14 to a prescribed concentration. The pump cell 31 has a pair of electrodes 32 and 33, which are an upper electrode and a lower electrode, and the solid electrolytic element 12 is disposed between the electrodes 32 and 33. In particular, the electrode 32, which is located near the first chamber 14, is a NOx inactive electrode (an electrode which hardly decomposes the NOx). When a voltage is applied between the electrodes 32 and 33, the pump cell 31 decomposes the oxygen in the first chamber 14 and discharges the oxygen from the electrode 33 toward the air path 22.

In the solid electrolytic element 11, the monitor cell 34 and the sensor cell 35 are located to face the second chamber 16. The monitor cell 34 generates an electromotive force depending on the residual oxygen concentration in the second chamber 16 or a current output when being applied by a voltage, after a surplus oxygen is discharged by the pump cell 31. The sensor cell 35 detects the NOx concentration of the gas in the second chamber 16. In the present embodiment, the pump cell 31 is a first cell and the monitor cell 34 and the sensor cell 35 are second cells. The monitor cell 34 detects the residual oxygen concentration in the second chamber 16 as a concentration of a specific component and the sensor cell 35 detects the NOx concentration in the second chamber 16 as the concentration of the specific component.

The monitor cell 34 and the sensor cell 35 are disposed to be adjacent to each other, and have electrodes 36 and 37 placed at positions near the second chamber 16 and a common electrode 38 placed at a position near the air path 18. In other words, the monitor cell 34 includes the solid electrolytic element 11, and the electrode 36 and the common electrode 38 which are located opposite to each other with the solid electrolytic element 11 disposed between them, and similarly the sensor cell 35 includes the solid electrolytic element 11, and the electrode 37 and the common electrode 38 which are located opposite to each other with the solid electrolytic element 11 disposed between them. While the electrode 36 of the monitor cell 34 (an electrode placed at a position near the second chamber 16) is made of a precious metal inactive to NOx such as Au—Pt, the electrode 37 of the sensor cell 35 (an electrode placed at a position near the second chamber 16) is made of a precious metal active to NOx such as platinum Pt or rhodium Rh. In convenience, the monitor cell 34 and the sensor cell 35 are located at the front and rear positions in a flow direction of the exhaust gas as shown in drawings, but actually the cells 34 and 35 are located at the same position in the flow direction of the exhaust gas. In this case, the flow direction of the exhaust gas is parallel to the longitudinal direction of the sensor element 10a.

The pump cell 31, the monitor cell 34, and the sensor cell 35 are arranged in the longitudinal direction of the sensor element 10a. The pump cell 31 is located at a position near the front end of the sensor element 10a and the monitor cell 34 and the sensor cell 35 are located at positions near the base end of the sensor element 10a (near a position where the exhaust pipe 52 is attached).

In the sensor element 10a having the above configuration, the exhaust gas is introduced into the first chamber 14 through the porous diffusion layer 17 and the exhaust-gas introduction port 11a. When the exhaust gas passes through a position in the vicinity of the pump cell 31, a pump cell voltage Vp is applied between the pump cell electrodes 32 and 33, a decomposition reaction occurs, and the oxygen flows in and out through the pump cell 31 according to the oxygen concentration in the first chamber 14. In this case, since the electrode 32 placed at a position near the first chamber 14 is an electrode inactive to NOx, in the pump cell 31 the NOx in the exhaust gas is not decomposed but only the oxygen is decomposed and discharged from the electrode 33 to the air path 22. According to the above operation of the pump cell 31, the oxygen concentration in the first chamber 14 is maintained at a state where the oxygen concentration is in a prescribed low level.

The gas (a gas after the oxygen concentration has been adjusted) passed a position in the vicinity of the pump cell 31 flows into the second chamber 16 and an output occurs in the monitor cell 34 depending on the residual oxygen concentration of the gas. An output of the monitor cell 34 that is a monitor cell output is detected as a monitor cell current Im by applying prescribed monitor cell voltage Vm between the monitor cell electrodes 36 and 38. When a sensor cell voltage Vs that is prescribed is applied between the sensor cell electrodes 37 and 38, the NOx in the gas is reduced and decomposed, and the oxygen generated at the same time is discharged from the electrode 38 to the air path 18. In this case, the NOx concentration of the exhaust gas is detected according to the current (sensor cell current Is) flowing through the sensor cell 35.

A sensor control circuit 40 includes a microcomputer 41 which is a main component of a sensor control, and a circuit part which includes a voltage applying section, a current detecting section, etc. The microcomputer 41 and the circuit part control the pump cell voltage Vp that is applied between the electrodes 32 and 33 of the pump cell 31, the monitor cell voltage Vm that is applied between the electrodes 36 and 38 of the monitor cell 34, and the sensor cell voltage Vs that is applied between the electrodes 37 and 38 of the sensor cell 35. The microcomputer 41 sequentially receives detected values of a pump cell current Ip, the monitor cell current Im, and the sensor cell current Is. In this case, the detected values correspond to the detection signals. The microcomputer 41 calculates the oxygen concentration of the exhaust gas and the NOx concentration of the exhaust gas based on the detected values. The microcomputer 41 may be provided, for example, in the ECU 60 as shown in FIG. 2.

The microcomputer 41 receives the detected values from the cells through an A/D converter that is not shown. In this case, a current within a current detection range preset at each of the above cells is detected as a detected current value, the detected current value is converted to a converted value within a voltage conversion range of the A/D converter, and the converted value is transmitted to the microcomputer 41. In the present embodiment, the current detection range corresponds to a concentration detection range, and the voltage conversion range is, for example, 0 to 5 V.

Figure 3:
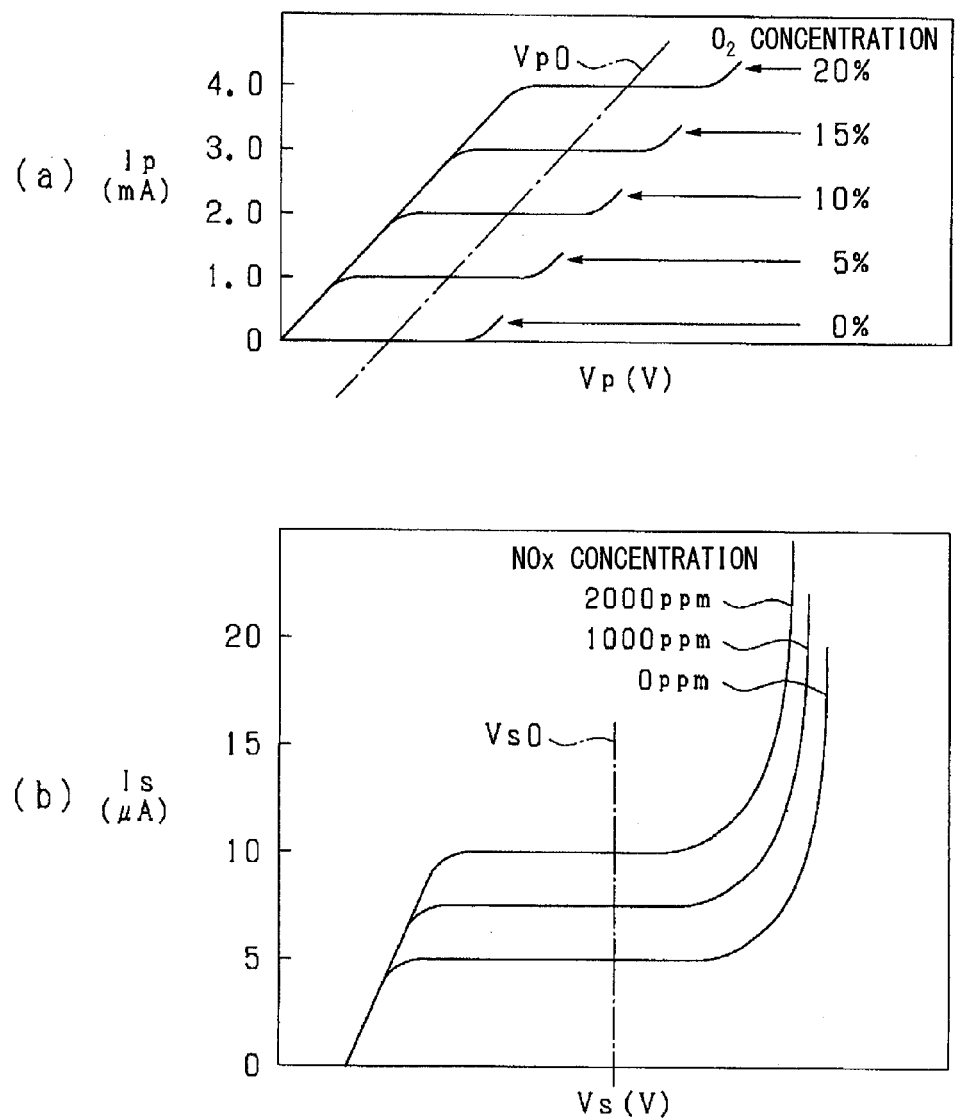
FIG. 3 is a graph showing output characteristics of the NOx sensor which correspond to an oxygen concentration and a NOx concentration.

Next, output characteristics of the NOx sensor 10 will be described referring to FIG. 3. FIG. 3 ($a$) is a graph showing output characteristics of the pump cell 31 (V-I characteristics) and FIG. 3 ($b$) is a graph showing output characteristics of the sensor cell 35 (V-I characteristics). As shown in FIG. 3 (*a*), a horizontal axis denotes the pump cell voltage Vp and a vertical axis denotes the pump cell current Ip. As shown in FIG. 3 (*b*), a horizontal axis denotes the sensor cell voltage Vs and a vertical axis denotes the sensor cell current Is.

As shown in FIG. 3 (*a*), a flat portion almost parallel to a voltage axis (the horizontal axis) is a limiting current region which specifies the pump cell current Ip, and an increase or a decrease of the pump cell current Ip changes in accordance with the oxygen concentration of the exhaust gas. In other words, when the oxygen concentration of the exhaust gas increases, the pump cell current Ip increases. When the oxygen concentration of the exhaust gas decreases, the pump cell current Ip decreases. When the oxygen concentration increases, the limiting current region shifts toward a higher voltage side, and accordingly an applied voltage characteristics (an applied voltage line Vp0) which determines the pump cell voltage Vp shifts toward the higher voltage side. A slope region with a voltage lower than the limiting current region is a resistance control region. The slope of the resistance control region depends on an element temperature. When the element temperature is lower, the slope is smaller.

As shown in FIG. 3 (*b*), a flat portion almost parallel to a voltage axis (the horizontal axis) is a limiting current region which specifies the sensor cell current Is and an increase or a decrease of the sensor cell current Is changes in accordance with the NOx concentration of the exhaust gas. In other words, when the NOx concentration of the exhaust gas increases, the sensor cell current Is increases. When the NOx concentration of the exhaust gas decreases, the sensor cell current Is decreases. The sensor cell voltage Vs is set to a prescribed value Vs0 where the sensor cell current Is corresponding to a prescribed NOx concentration can be detected in the limiting current region. Similar to the output characteristics of the pump cell 31, a slope region with a voltage lower than the limiting current region is a resistance control region, and a slope of the resistance control region is smaller when the element temperature is lower.

A current output of the pump cell 31 and a current output of the sensor cell 35 are different in a request of magnitude. The pump cell 31 is requested to output the pump cell current Ip at a mA level, and the sensor cell 35 is requested to output the sensor cell current Is at a µA level. A maximum detection range of the NOx concentration is 0 to 3000 ppm.

In the sensor control circuit 40 according to the present embodiment, an oxygen discharge amount that is an amount of the oxygen that is discharged is temporarily forcibly changed by the pump cell 31, and the sensitivities of the sensor cell 35 and the monitor cell 34 are corrected according to the amount of change of the output of the sensor cell 35 and the amount of change of the monitor cell output at the same time. According to the present embodiment, the output of the sensor cell 35 is referred to as a sensor cell output. Specifically, in the NOx sensor 10, when the oxygen discharge amount (an oxygen pumping amount) at the pump cell 31 is forcibly changed, the oxygen concentration (an oxygen concentration in the second chamber 16) after the oxygen is discharged changes according to a change of the oxygen discharge amount, and a change occurs in the sensor cell output and the monitor cell output according to an amount of a change of the oxygen concentration. However, when a sensitivity error occurs in the sensor cell 35 or the monitor cell 34 due to an individual difference, a deterioration or the like, the amount of the change of the sensor cell output/the monitor cell output which corresponds to the change of the oxygen concentration will be different from the amount of the change of when the sensitivity error does not occur. The amount of the change of the sensor cell output/the monitor cell output of when the oxygen pumping amount is changed is calculated, the sensor cell output (corresponding to the NOx concentration) and the monitor cell output (corresponding to the residual oxygen concentration) are corrected based on the amount of the change of the sensor cell output/the monitor cell output.

In particular, in the present embodiment, in order to suppress a decreasing of an accuracy in a sensor detection signal generated due to a variation in the amount of the oxygen discharged by the pump cell 31, an actual discharge amount that is an actual oxygen pumping amount is calculated after an instruction changing the oxygen pumping amount is sent, and the correction values of the sensor cell output and the monitor cell output are calculated by using the actual discharge amount. Specifically, when an instruction changing the pump cell voltage Vp is sent, a change amount ΔIp of the pump cell current which corresponds to the actual oxygen pumping amount is calculated based on the pump cell currents Ip before and after the instruction is sent. In the present embodiment, the change amount ΔIp is also called a change amount ΔIp of a pump cell output. According to the present embodiment, the output of the pump cell 31 is referred to as the pump cell output. The correction values of the sensor cell output and the monitor cell output are calculated by using the change amount ΔIp of the pump cell output.

Figure 4:
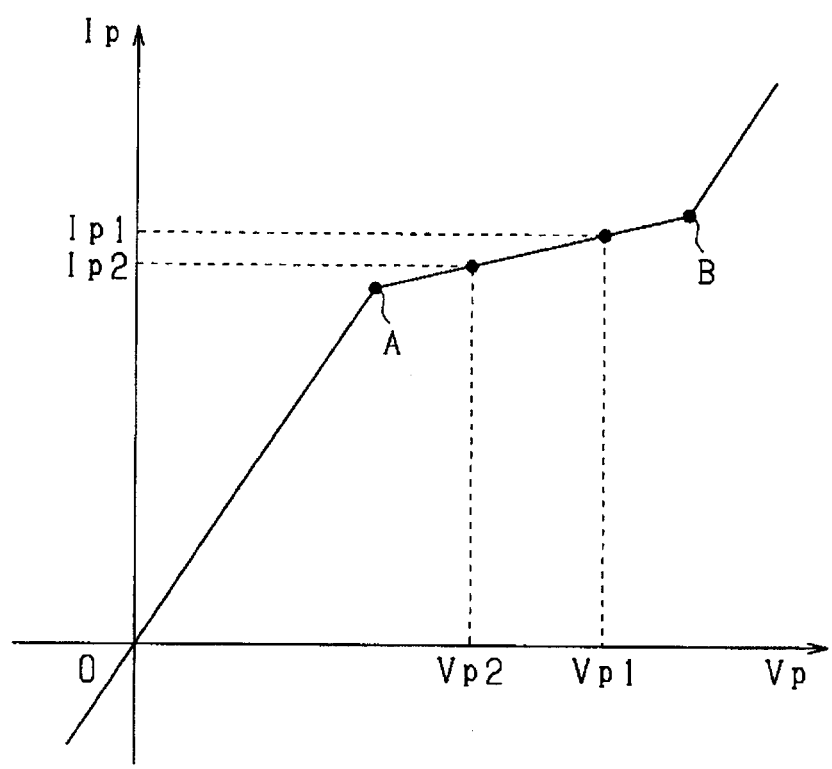
FIG. 4 is a graph showing details of output characteristics of a pump cell.

Next, the output characteristics of the pump cell 31 will be described in detail referring to FIG. 4. In the output characteristics shown in FIG. 4, a region from a point A to a point B is a limiting current region and the limiting current region is a region in which an output of the pump cell current Ip is almost constant relative to the pump cell voltage Vp of the horizontal axis. However, looking at the graph more carefully, the limiting current region has a slope, which means that a change of the pump cell voltage Vp causes the pump cell current Ip to change. For example, when the pump cell voltage Vp is changed from Vp1 to Vp2, the pump cell current Ip changes from Ip1 to Ip2. In this case, since the pump cell current Ip decreases by (Ip1−Ip2), the amount of the oxygen discharged by the pump cell 31 decreases, and the residual oxygen concentration in the second chamber 16 of the NOx sensor 10 increases. Accordingly, the sensor cell output and the monitor cell output change. The pump cell current Ip can be considered as an ability of the pump cell 31 to discharge the oxygen, and the ability that is an oxygen discharge ability is decreased due to a decrease in Ip.

In the output characteristics of the pump cell 31, a difference in the slope of the limiting current region may occur. When the difference is generated, the difference may affect the change amount of the pump cell current Ip (actual oxygen discharge amount relative to an instruction discharging the oxygen) and also decrease an accuracy in a correction value calculation. An individual difference of the pump cell 31, an aging change such as a deterioration, an active state difference, and so on, may lead to the difference in the slope of the limiting current region. As described above, the change amount ΔIp of the pump cell output is calculated based on the pump cell currents Ip before and after Vp is changed, change amounts ΔIs and ΔIm of the outputs of the sensor cell 35 and the monitor cell 34 are calculated, and output correction values of the sensor cell 35 and the monitor cell 34 are calculated by using ΔIp, ΔIs, and ΔIm. Therefore, even when a difference occurs in the slope of the limiting current region, correction values which indicate the difference can be calculated.

In the present embodiment, the sensor cell 35 detects the NOx concentration up to about 3000 ppm and it is preferable that the oxygen concentration is changed within a range in which the NOx concentration can be detected. Therefore, a change of the pump cell voltage Vp may be performed within the limiting current region in the output characteristics of the pump cell 31.

Figure 5:
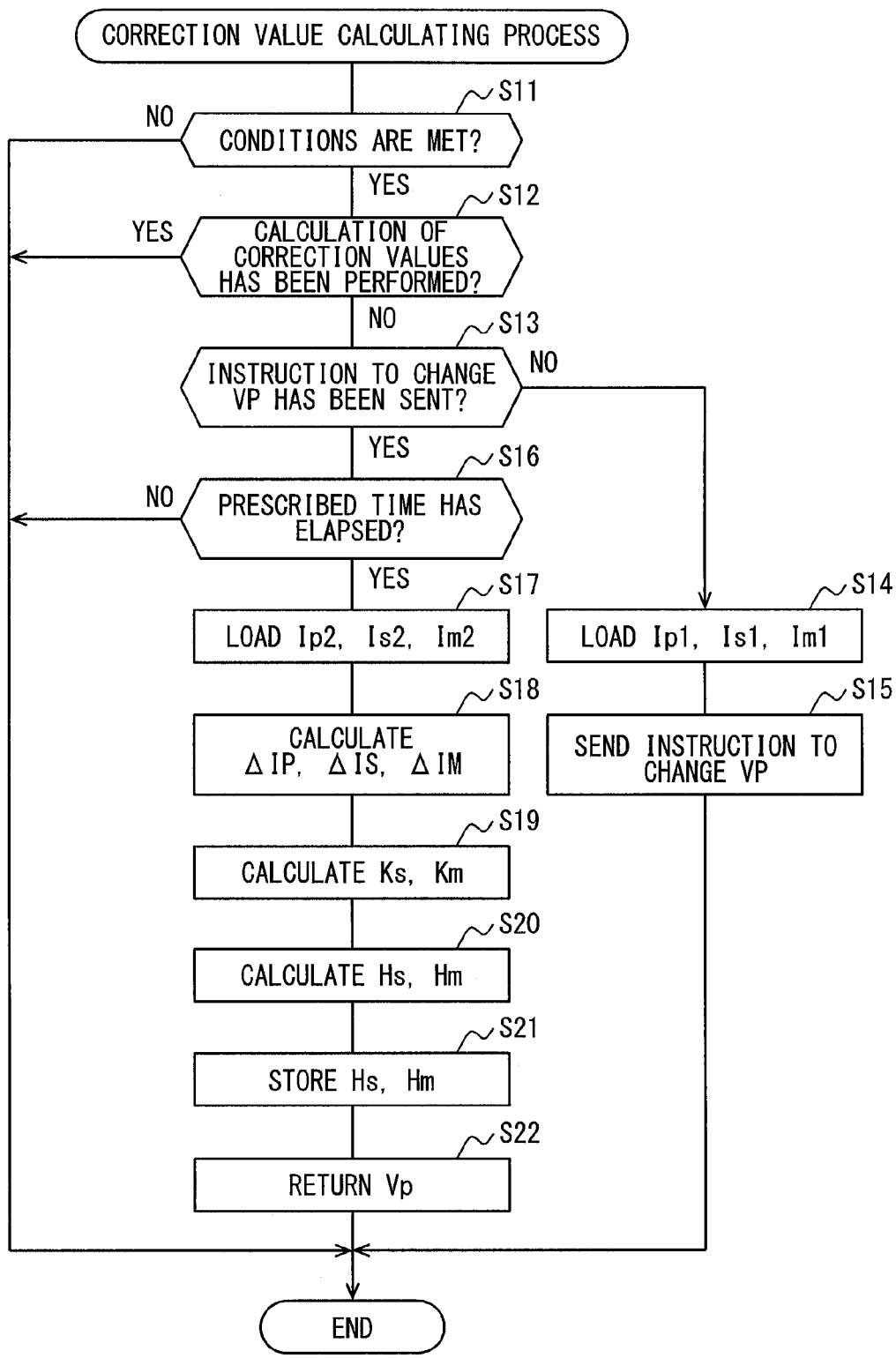
FIG. 5 is a flowchart showing a correction value calculation process.

FIG. 5 is a flowchart showing the correction value calculation process. The correction value calculation process is repeatedly performed in a prescribed cycle by the microcomputer 41.

As shown in FIG. 5, at S11 the microcomputer 41 determines whether or not the conditions to calculate sensor output correction values are met. In the present embodiment, the sensor output correction values are correction values of outputs of the sensor cell 35 and the monitor cell 34. The conditions include a condition (i) that the NOx sensor 10 is in a prescribed active state, a condition (ii) that the engine 50 is in a fuel cut state, a condition (iii) that a prescribed time has passed since a fuel cut starts, and a condition (iv) that the pump cell 31 is in a normal state. In the condition (iii), the prescribed time corresponds to a waiting time until the sensor output becomes stable. When the conditions are all met, the microcomputer 41 determines that the conditions to calculate correction values are met. It is optional to determine whether or not the pump cell 31 is in the normal state. One example is that a normality determination is determined according to whether or not the pump cell current Ip is a prescribed value (for example, a value corresponding to the atmosphere) when the oxygen concentration is a known state (for example, an atmospheric state).

At S12 the microcomputer 41 determines whether or not a calculation of correction values has been performed after an ignition switch of a vehicle is turned ON. In this case, the ignition switch is equivalent to a power switch. When the answer is NO at S11 or is YES at S12, the microcomputer 41 ends the process. When the answer is YES at S11 and is NO at S12, the microcomputer 41 proceeds to S13.

At S13 the microcomputer 41 determines whether or not an instruction changing the pump cell voltage Vp has been sent. When the microcomputer 41 determines that an instruction changing Vp has not been sent yet, the microcomputer 41 proceeds to S14 and loads the pump cell current Ip1, the sensor cell current Is1, and the monitor cell current Im1 before Vp is changed. At S15 the microcomputer 41 sends an instruction changing the pump cell voltage Vp. In this case, a change amount of the pump cell voltage Vp causes a decrease in the oxygen concentration which is equivalent to 3000 ppm in the NOx concentration. Alternatively the change amount of the pump cell voltage Vp may cause a decrease in the oxygen concentration which is equivalent to less than 3000 ppm. For example, the change amount of the pump cell voltage Vp may cause a decrease in the oxygen concentration which is equivalent to 2000 to 3000 ppm.

When the microcomputer 41 determines at S13 that an instruction changing Vp has been sent, the microcomputer 41 proceeds to S16 and determines whether or not a prescribed time has elapsed since a change of the pump cell voltage Vp occurs. In the present embodiment, the prescribed time corresponds to a convergence time for each current. When the microcomputer 41 determines that the prescribed time has passed since a change of Vp occurs, the microcomputer 41 proceeds to S17, and loads the pump cell current Ip2, the sensor cell current Is2, and the monitor cell current Im2, after the change of Vp occurs. At S18 the microcomputer 41 calculates output change amounts $\Delta Ip$, $\Delta Is$, and $\Delta Im$ before and after the change of Vp occurs for the pump cell 31, sensor cell 35, and the monitor cell 34 based on equations (1), (2), and (3) below, respectively:

$$\Delta Ip = Ip1 - Ip2 \tag{1}$$

$$\Delta Is = Is2 - Is1 \tag{2}$$

$$\Delta Im = Im2 - Im1 \tag{3}$$

In this case, the output change amount $\Delta Ip$ of the pump cell 31 is calculated as the amount of the decrease of the pump cell current Ip, and the output change amounts $\Delta Is$ and $\Delta Im$ of the sensor cell 35 and the monitor cell 34 are calculated as the amounts of increases of the sensor cell current Is and the monitor cell current Im.

Then, at S19 the microcomputer 41 calculates output sensitivity values Ks and Km of the sensor cell 35 and the monitor cell 34 by dividing output change amounts $\Delta Is$ and $\Delta Im$ of the sensor cell 35 and the monitor cell 34 by the output change amount $\Delta Ip$ of the pump cell 31.

Specifically, the microcomputer 41 calculates the output sensitivity values Ks and Km based on equations (4) and (5) below.

$$Ks = \Delta Is / \Delta Ip \tag{4}$$

$$Km = \Delta Im / \Delta Ip \tag{5}$$

Then, at S20 the microcomputer 41 calculates the output correction values Hs and Hm of the cells 35 and 34 using the output sensitivity values Ks and Km of the cells 35 and 34 calculated at S19 and sensitivity reference values Rs and Rm of the cells 35 and 34 based on equations (6) and (7) below.

$$Hs = Ks / Rs \tag{6}$$

$$Hm = Km / Rm \tag{7}$$

The sensitivity reference values Rs and Rm are set according to a Vp change amount and are predetermined as the sensitivity values in an initial state in which a deterioration has not occurred yet. According to the present embodiment, the Vp change amount is an amount of the change of Vp.

Then, at S21 the microcomputer 41 stores the output correction values Hs and Hm calculated as the above as learning values in a backup memory. The backup memory may be an EEPROM (registered trademark) provided in the ECU 60. Then, at S22 the microcomputer 41 resets the pump cell voltage Vp to the voltage value before the change.

In a normal control, the output correction values Hs and Hm are loaded as necessary, and a correction of the sensor cell output and the monitor cell output is performed by the output correction values Hs and Hm. In other words, in this case, a correction of the NOx concentration and the residual oxygen concentration is performed by the output correction values Hs and Hm. The sensor cell output and the monitor cell output may be converted into physical values based on equations (8) and (9) below.

$$\text{Physical value of sensor cell output} = \text{Sensor cell output} \times Gs \times Hs \tag{8}$$

$$\text{Physical value of monitor cell output} = \text{Monitor cell output} \times Gm \times Hm \tag{9}$$

In this case, Gs and Gm denote conversion coefficients converting the sensor cell output and the monitor cell output into physical values, respectively. In the present embodiment, the output correction values Hs and Hm are the learning values.

Figure 6:
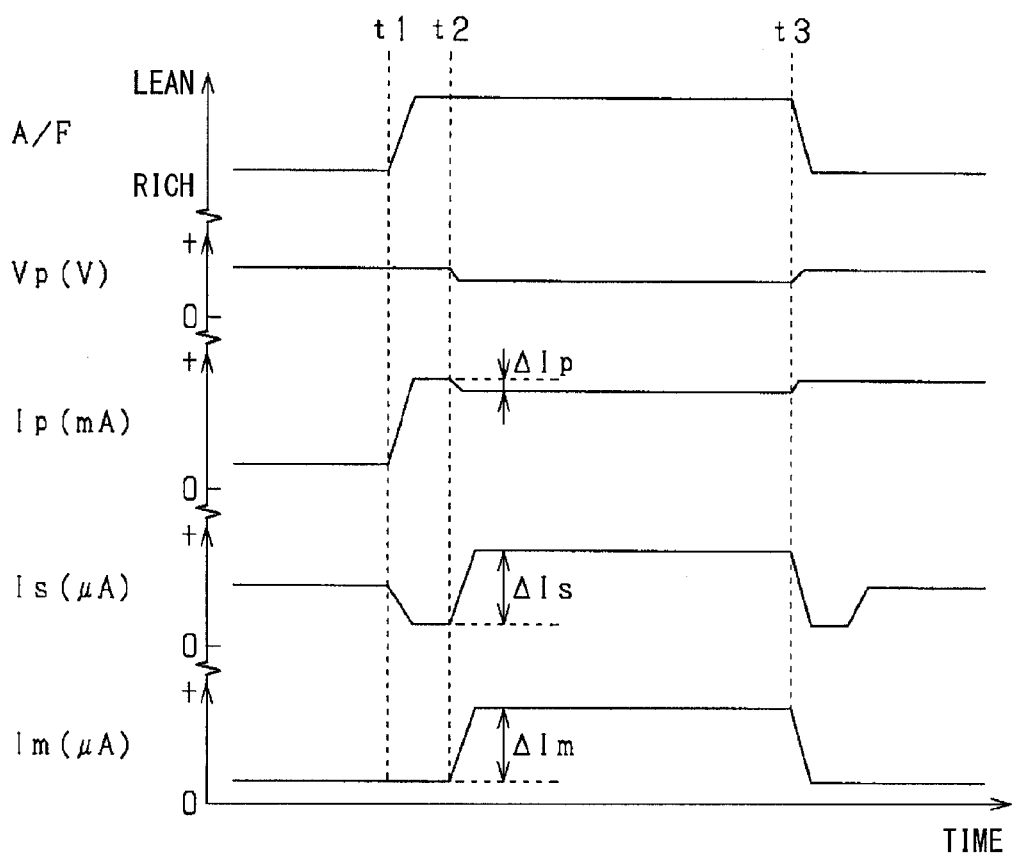
FIG. 6 is a time chart explaining a calculation of correction values more specifically.

FIG. 6 is a time chart explaining a calculation of correction values more specifically.

As shown in FIG. 6, before timing t1, an air-fuel ratio is a prescribed ratio (a lean air-fuel ratio), the pump cell 31 outputs the pump cell current Ip depending on the oxygen concentration in the first chamber 14, the sensor cell 35 outputs the sensor cell current Is depending on the NOx concentration and the oxygen concentration in the second chamber 16, and the monitor cell 34 outputs the monitor cell current Im depending on the oxygen concentration in the second chamber 16.

At timing t1, the engine 50 enters the fuel cut state and the air-fuel ratio immediately shifts to a lean side (an atmosphere side). Accordingly, the pump cell current Ip increases up to a value corresponding to the atmosphere. Further, the NOx in the exhaust gas decreases (becomes almost zero), Is is decreased and becomes equal to Im. In other words, in the fuel cut state, the sensor cell current Is which is not affected by the NOx concentration can be obtained. As shown in FIG. 6, even when the air-fuel ratio shifts to the atmosphere side, the pump cell voltage Vp is constant. However, the pump cell voltage Vp may be changed depending on the air-fuel ratio as shown in FIG. 3 (a).

Then, at timing t2 that a prescribed time has elapsed after the fuel cut starts, an instruction decreasing the pump cell voltage Vp is sent and consequently the currents Ip, Is, and Im change. Then, the output change amounts ΔIp, ΔIs, and ΔIm are calculated based on the currents Ip, Is, and Im before and after the change of Vp occurs. Furthermore, the output sensitivity values Ks and Km and the output correction values Hs and Hm of the sensor cell 35 and the monitor cell 34 are calculated using the output change amounts ΔIp, ΔIs, ΔIm, etc. In this case, since the engine 50 is in the fuel cut state and the NOx is not being detected, the sensor cell current Is can be changed by fully utilizing a range of a NOx detection, and the accuracy of the calculation of the output sensitivity values Ks and Km and the output correction values Hs and Hm can be improved.

Then, at timing t3, the fuel cut is ended and the pump cell voltage Vp is returned to the voltage value before the change.

Figure 7:
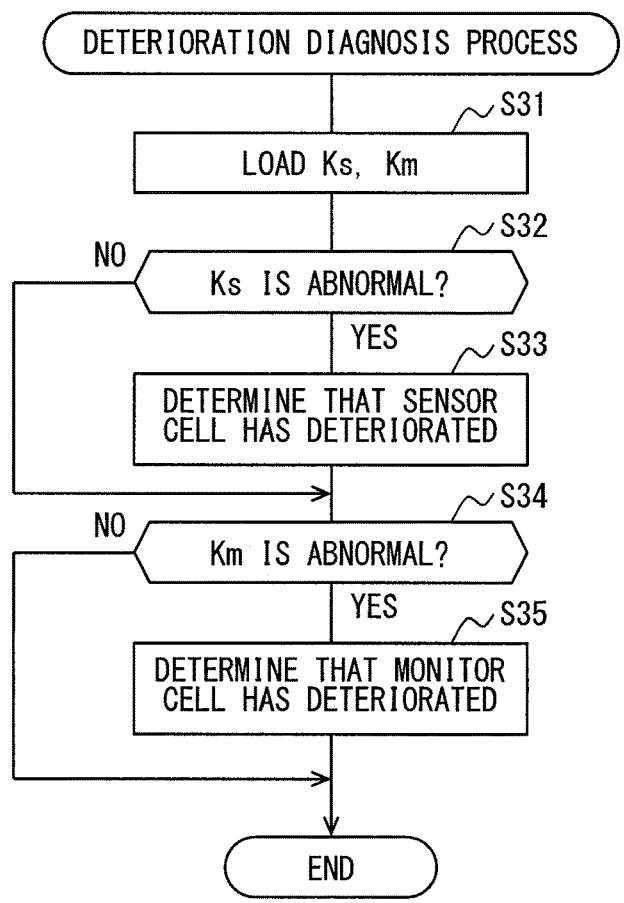
FIG. 7 is a flowchart showing a deterioration diagnosis process of a sensor cell and a monitor cell.

A deterioration diagnosis of the sensor cell 35 and the monitor cell 34 can be performed by using the output change amounts ΔIp, ΔIs, and ΔIm before and after the instruction changing Vp is sent. In the present embodiment, the deterioration diagnosis of the sensor cell 35 and the monitor cell 34 is performed using the output sensitivity values Ks and Km calculated based on the output change amounts ΔIp, ΔIs, and ΔIm of the cells. FIG. 7 is a flowchart showing a deterioration diagnosis process of the sensor cell 35 and the monitor cell 34. The deterioration diagnosis process is repeatedly performed in a prescribed cycle by the microcomputer 41.

As shown in FIG. 7, at S31 the microcomputer 41 loads the output sensitivity values Ks and Km of the sensor cell 35 and the monitor cell 34. The output sensitivity values Ks and Km are calculated based on the output change amounts ΔIp, ΔIs, and ΔIm of the cells by a method described above referring to FIG. 5. Then, at S32 the microcomputer 41 determines whether or not the output sensitivity value Ks of the sensor cell 35 is abnormal. When the microcomputer 41 determines that the output sensitivity value Ks is abnormal, the microcomputer 41 proceeds to S33 and determines that the sensor cell 35 has deteriorated. A normal range of the output sensitivity value Ks is predetermined. When the output sensitivity value Ks is above an upper limit of the normal range or below a lower limit of the normal range, the output sensitivity value Ks is determined to be abnormal.

At S34 the microcomputer 41 determines whether or not the output sensitivity value Km of the monitor cell 34 is abnormal. When the microcomputer 41 determines that the output sensitivity value Km is abnormal, the microcomputer 41 proceeds to S35 and determines that the monitor cell 34 has deteriorated. A normal range of the output sensitivity value Km is predetermined. When the output sensitivity value Km is above an upper limit of the normal range or below a lower limit of the normal range, the output sensitivity value Km is determined to be abnormal.

As parameters of an abnormality diagnosis, not only the output sensitivity values Ks and Km but also the output change amounts ΔIs and ΔIm or the output correction values Hs and Hm may be used.

When the amount of the oxygen discharged by the pump cell 31 is changed, the output change amount ΔIp (equivalent to the actual discharge amount) caused by the change is calculated and at the same time the output change amounts ΔIs and ΔIm of the sensor cell 35 and the monitor cell 34 are calculated. Based on the output change amounts ΔIp, ΔIs, and ΔIm of the cells, an output correction and the deterioration diagnosis of the sensor cell 35 and the monitor cell 34 are performed. In this case, an amount of the oxygen actually discharged in response to the instruction discharging the oxygen can be monitored to calculate correction values (concentrations) and to perform the deterioration diagnosis, and an accuracy in a calculation and the deterioration diagnosis can be improved. As a consequence, the NOx sensor 10 can be controlled properly.

In the calculation of the output correction values, the pump cell voltage Vp is temporarily changed in a condition that the engine 50 is in the fuel cut state. In this case, in the fuel cut state of the engine 50, the NOx concentration is zero and the oxygen discharge amount can be changed utilizing a whole range of the NOx concentration detection in the sensor cell 35. Specifically, when an upper limit of the NOx concentration detection is 3000 ppm, the oxygen in the amount equivalent to the upper limit of the NOx concentration detection can be pumped. Therefore, a reliability of the output correction can be improved. Similarly, a reliability of the deterioration diagnosis can be improved.

Furthermore, in the fuel cut state, unlike a state other than the fuel cut state, the output correction and the deterioration diagnosis can be performed properly regardless of a purification performance of the exhaust gas purifier 53 (catalyst). In other words, in a configuration in which the NOx sensor 10 is located downstream of the exhaust gas purifier 53 according to the present embodiment, the amount of the NOx which flows out downstream of the exhaust gas purifier 53 may differ depending on a condition of the purification of the exhaust gas purifier 53. However, in the fuel cut state, the output correction and the deterioration diagnosis can be performed properly regardless of the condition of the purification of the exhaust gas purifier 53. Further, an advantage that the output correction and the deterioration diagnosis can be performed at any time regardless of the condition of the exhaust purifying catalyst (for example, active or inactive, etc.) can be obtained.

Furthermore, in the fuel cut state, since the NOx concentration is maintained to be constant; it can be avoided that an output correction value is erroneously calculated due to a variation of the NOx concentration and the deterioration diagnosis is erroneously determined.

Since a calculation of the output change amounts ΔIp, ΔIs, and ΔIm, the calculation of the output correction values, and the deterioration diagnosis are performed in a condition that the pump cell 31 is normal, the reliability of the calculation of the output correction values and the deterioration diagnosis can be improved.

Figure 9:
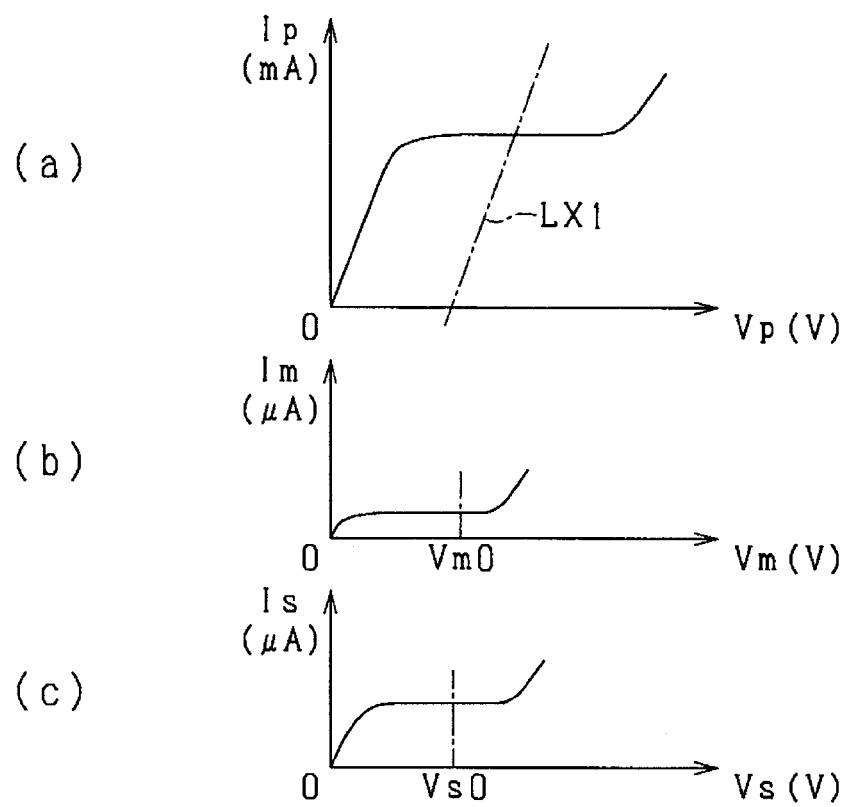
FIG. 9 is a graph showing the output characteristics of the NOx sensor in a case where the oxygen concentration and the NOx concentration are constant.

Next, characteristics of the pump cell 31, the monitor cell 34, and the sensor cell 35 will be described referring to FIG. 9. FIG. 9 (a) to FIG. 9 (c) show basic characteristics in a condition that the oxygen concentration and the NOx concentration are constant.

FIG. 9 (a) is a V-I characteristic graph showing the relationship between the pump cell voltage Vp and the pump cell current Ip as a pump cell characteristic. As shown in FIG. 9 (a), a flat portion almost parallel to a voltage axis (a horizontal axis) is a limiting current region which specifies the pump cell current Ip and an increase or a decrease of the pump cell current Ip changes in accordance with the oxygen concentration of the exhaust gas. In other words, when the oxygen concentration of the exhaust gas increases, the pump cell current Ip increases. When the oxygen concentration of the exhaust gas decreases, the pump cell current Ip decreases. When the oxygen concentration increases, the limiting current region shifts toward a higher voltage side, and accordingly an applied voltage characteristics (an applied voltage line LX1) which determines the pump cell voltage Vp shifts toward the higher voltage side. A slope region with a voltage lower than the limiting current region is a resistance control region. The slope of the resistance control region depends on an element temperature. When the element temperature is lower, the slope is smaller.

FIG. 9 (b) is a V-I characteristic graph showing the relationship between the monitor cell voltage Vm and the monitor cell current Im as a monitor cell characteristic. As shown in FIG. 9 (b), a flat portion almost parallel to a voltage axis (a horizontal axis) is a limiting current region which specifies the monitor cell current Im and an increase or a decrease of the monitor cell current Im changes in accordance with the residual oxygen concentration in the second chamber 16. In other words, when the residual oxygen concentration in the second chamber 16 increases, the monitor cell current Im increases. When the residual oxygen concentration decreases, the monitor cell current Im decreases. The monitor cell voltage Vm is set to a prescribed value Vm0 where the monitor cell current Im corresponding to a prescribed oxygen concentration can be detected in the limiting current region.

FIG. 9 (c) is a V-I characteristic graph showing the relationship between the sensor cell voltage Vs and the sensor cell current Is as a sensor cell characteristic. As shown in FIG. 9 (c), a flat portion almost parallel to a voltage axis (a horizontal axis) is a limiting current region which specifies the sensor cell current Is and an increase or a decrease of the sensor cell current Is changes in accordance with the NOx concentration of the exhaust gas (in the second chamber 16). In other words, when the NOx concentration of the exhaust gas increases, the sensor cell current Is increases. When the NOx concentration of the exhaust gas decreases, the sensor cell current Is decreases. However, in this case, since not only the NOx but also the residual oxygen exist in the second chamber 16, the sensor cell current Is depends on the amounts of the NOx and the residual oxygen. The sensor cell voltage Vs is set to a prescribed value Vs0 where the sensor cell current Is corresponding to a prescribed NOx concentration can be detected in the limiting current region.

In the NOx sensor 10, since the monitor cell current Im depends on the amount of the oxygen in the second chamber 16 and the sensor cell current Is depends on the amounts of the oxygen and the NOx in the second chamber 16, Im should be smaller than Is in a comparison between the monitor cell current Im and the sensor cell current Is. However, when the NOx sensor 10 has an abnormality, it is possible that the relationship in magnitude between Im and Is is reversed. In the present embodiment, the comparison is performed between the monitor cell current Im and the sensor cell current Is and whether or not the NOx sensor 10 has an abnormality is determined based on a result of the comparison.

Figure 10:
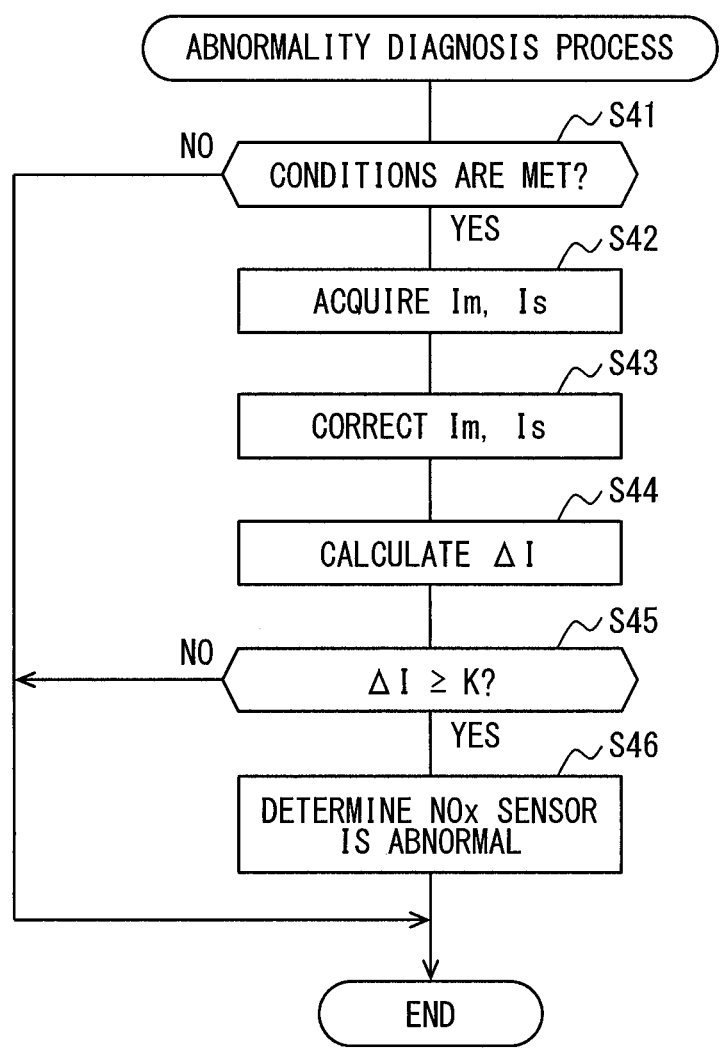
FIG. 10 is a flowchart showing an abnormality diagnosis process of the NOx sensor.

FIG. 10 is a flowchart showing an abnormality diagnosis process of the NOx sensor 10. The abnormality diagnosis process is repeatedly performed in a prescribed cycle by the microcomputer 41.

As shown in FIG. 10, at S41 the microcomputer 41 determines whether or not the conditions performing the abnormality diagnosis are met. The conditions include a condition (v) that the NOx sensor 10 is active and a condition (vi) that the engine 50 is running in a lean combustion mode. When the microcomputer 41 determines that the conditions are all met, the microcomputer 41 determines that the conditions performing the abnormality diagnosis are met, and proceeds to the next step S42.

At S42 the microcomputer 41 acquires the monitor cell current Im and the sensor cell current Is. At S43 the microcomputer 41 corrects characteristic deviations of the monitor cell current Im and the sensor cell current Is. Specifically, in the NOx sensor 10, it is possible that a characteristic deviation is generated due to an individual difference (an initial characteristic deviation) or a characteristic deviation is generated due to an aging change (a characteristic deterioration), and it is possible that the accuracy of the sensor abnormality diagnosis is decreased in a case where at least one of the above deviations is generated. Therefore, the current values are corrected so as to suppress a decreasing in the diagnosis accuracy generated due to the characteristic deviation.

Specifically, the monitor cell current Im and the sensor cell current Is are loaded when the engine is stopped in a sensor active state (for example, just after the ignition switch IG is turned off) and a difference of Im or Is from a predetermined reference value is calculated and stored as a characteristic error (correction value). Alternatively, an amount of a sulfur poisoning caused by a prolonged use of the NOx sensor 10 (or an amount of an oil additive such as Pb) may be estimated, and the characteristic error (correction value) may be set depending on an estimated amount. For example, the characteristic error (correction value) may be set according to an integrated value of a cumulative amount of a fuel injection, a cumulative amount of the exhaust gas, a total travel distance of the vehicle, etc. At S43 the microcomputer 41 corrects Im and Is by the characteristic errors (correction values) every time. A correction of the characteristic deviation may be performed for at least either Im or Is or the correction may be performed for only Im or only Is.

Then, at S44 the microcomputer 41 subtracts the sensor cell Is from the monitor cell current Im to calculate an output difference ΔI. Specifically the microcomputer 41 calculates the output difference ΔI based on an equation (10) below.

$$\Delta I = Im - Is \quad (10)$$

The output difference ΔI corresponds to the relative difference of a monitor cell detected value from a sensor cell detected value. At S45 the microcomputer 41 determines whether or not the output difference ΔI is larger than or equal to a criterial value K. In this case, the criterial value K is a positive value. However, K may be zero.

When ΔI is smaller than K, the microcomputer 41 determines that the NOx sensor 10 is normal, and ends the present process. When the microcomputer 41 determines that ΔI is larger than or equal to K, the microcomputer 41 proceeds to S46 and determines that the NOx sensor 10 has an abnormality. When the microcomputer 41 determines that the NOx sensor 10 has an abnormality, the microcomputer 41 performs various fail-safe processes including a storing of a diagnosis data and a stopping of a catalyst degradation diagnosis by using a NOx sensor output.

In the NOx sensor 10, the sensor cell current Is should be larger than the monitor cell current Im. When the sensor cell current Is is smaller than the monitor cell current Im, the NOx sensor 10 can be determined to have an abnormality. In such an abnormality diagnosis, a configuration of the NOx sensor 10 does not need to be altered. Thus, the abnormality diagnosis of the NOx sensor 10 can be performed without complicating the configuration. According to the present embodiment, the abnormality diagnosis of the NOx sensor 10 is referred to as a sensor abnormality diagnosis.

The characteristic deviations of the monitor cell current Im and the sensor cell current Is are corrected, and the corrected Im and Is are used to perform the sensor abnormality diagnosis. Therefore, even when the NOx sensor 10 has a characteristic deviation, an effect of the characteristic deviation can be suppressed and the accuracy of the abnormality diagnosis can be improved.

The sensor abnormality diagnosis is performed based on the monitor cell current Im and sensor cell current Is which are acquired when it is determined that the engine 50 is in the lean combustion state. When the engine 50 is in the lean combustion state, the exhaust gas always includes the NOx unlike in a stoichiometric combustion state or a rich combustion state. Therefore, since the lean combustion state is one of the conditions which should be met to perform the abnormality diagnosis, the accuracy of the abnormality diagnosis based on a comparison between the monitor cell current Im and the sensor cell current Is can be improved.

OTHER EMBODIMENTS

The above embodiment may be modified as follows.

(a) In the above embodiment, in the calculation of the output correction values, the pump cell voltage Vp is temporarily changed in a condition that the engine 50 is in the fuel cut state. Alternatively, the pump cell voltage Vp may be temporarily changed even when the engine 50 is not in the fuel cut state, in a condition that the NOx concentration of the exhaust gas is below a prescribed value (relatively low). In this case, the output correction values may be calculated in a condition that the NOx concentration is unlikely to vary. For example, the output correction values may be calculated when the exhaust gas purifying catalyst located upstream of the NOx sensor 10 is active and when the engine 50 is in an idle state.

When the NOx concentration is relatively lower, the sensor cell current Is before the change of Vp occurs is relatively smaller. Therefore, an amount where the sensor cell current Is can be increased becomes larger relative to an upper limit of the sensor cell current Is. In other words, a range of a forced change of the sensor cell current Is can be widened. Therefore, the reliability of the output correction can be improved.

Figure 8:
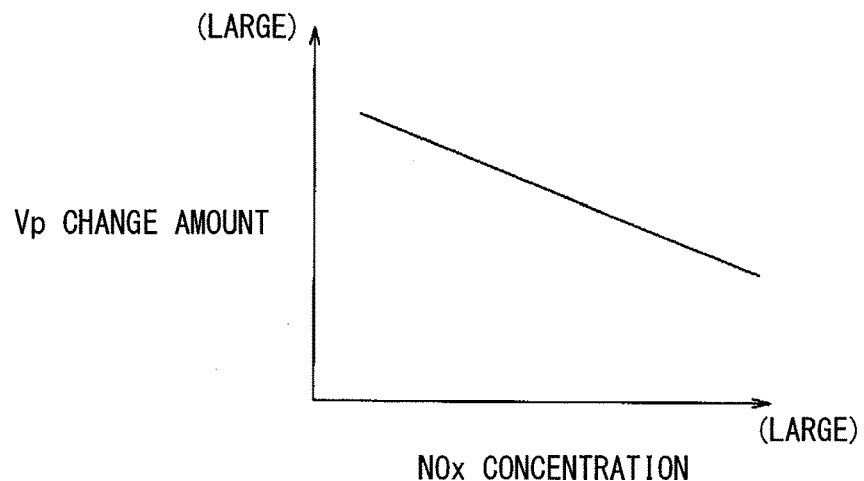
FIG. 8 is a graph showing the relationship between the NOx concentration and a Vp change amount.

(b) When the pump cell voltage Vp is temporarily forcibly changed in a case where the output correction values are calculated, the Vp change amount (the oxygen discharge amount) may be variably set depending on the NOx concentration every time. In this case, as shown in FIG. 8, when the NOx concentration (i.e., the sensor cell current Is before Vp is changed) is lower, the Vp change amount becomes larger. When the NOx concentration is higher, the Vp change amount becomes smaller. Also, the Vp change amount may be variably set depending on the residual oxygen concentration (i.e., the monitor cell current Im before Vp is changed). In this case, when the residual oxygen concentration is lower, the Vp change amount becomes larger.

In the above configuration, when an output range of the sensor cell 35 or the monitor cell 34 is limited, the output of the sensor cell or the monitor cell can be changed to a maximum limit while the sensor cell output or the monitor cell output is maintained to be within a prescribed output range after the change of Vp occurs. Therefore, the accuracy of the output correction and the deterioration diagnosis can be improved.

(c) In the above embodiment, the correction value calculation and the deterioration diagnosis are performed only once after the power switch of the vehicle is turned on. Alternatively, the correction value calculation and the deterioration diagnosis may be repeated every time that a prescribed condition is met. For example, the correction value calculation and the deterioration diagnosis may be performed at every predetermined time interval or every predetermined travel distance or every time that the engine 50 enters the fuel cut state.

(d) In the above embodiment, the calculation of the output correction values and the deterioration diagnosis are performed for both the sensor cell 35 and the monitor cell 34 of the NOx sensor 10. Alternatively, the calculation of the output correction values and the deterioration diagnosis may be performed for one of the sensor cell 35 and the monitor cell 34 of the NOx sensor 10. Alternatively, one of the calculation of the output correction values or the deterioration diagnosis may be performed.

(e) In the above embodiment, when the pump cell voltage Vp is temporarily changed in a case where the output correction values are calculated, the pump cell voltage Vp is decreased (the oxygen discharge amount is decreased). Alternatively, the pump cell voltage Vp may be increased (the oxygen discharge amount is increased).

(f) The configuration of the NOx sensor 10 may be different from the configuration shown in FIG. 1. For example, instead of a configuration in which the exhaust gas is introduced into the first chamber 14 through the exhaust-gas introduction port 11*a* provided in the solid electrolytic element 11, a diffusion resistance layer may be provided between the solid electrolytic elements 11 and 12 which are opposite to each other (for example, a part of the spacer 13 may be used as the diffusion resistance layer), and the exhaust gas may be introduced into the first chamber 14 through the diffusion resistance layer. In the above embodiment, the first chamber 14 and second chamber 16 used as gas chambers communicate with each other through the throttling part 15. Alternatively, the chambers 14 and 16 may be integrated into a single gas chamber without a throttling part.

(g) In the above embodiment, the sensor element of the NOx sensor 10 has a three-cell structure which includes the pump cell, the sensor cell, and the monitor cell. However, the three-cell structure may be modified. For example, the sensor element may have a two-cell structure which includes a pump cell and a sensor cell. In this case, the sensor cell is the second cell. When a monitor cell is used, the monitor cell may be an electrogenic cell which generates the electromotive force.

(h) The specific component which is an object of the detection may be neither the oxygen (the residual oxygen) nor the NOx. For example, the sensor may be a gas sensor detecting a HC or a CO in the exhaust gas as the object of the detection (the specific component). In this case, the pump cell discharges surplus oxygen from the exhaust gas and the sensor cell decomposes the exhaust gas into the HC and the CO and detects a HC concentration or a CO concentration after the surplus oxygen is discharged. Alternatively, the sensor may detect an ammonia concentration in a detected gas that is the gas that has been detected.

(i) The present disclosure may be embodied as a sensor control device applied to a gas sensor provided in an air intake path of an engine or a gas sensor used in a non-diesel engine such as a gasoline engine. The gas sensor may detect a gas other than the exhaust gas or may be used for a purpose other than use in a vehicle.

(j) In the above abnormality diagnosis process, the criterial value K of the abnormality diagnosis may be variably set depending on a condition every time. A concrete example is described below. FIG. 11 (a) and FIG. 11 (b) are flowcharts showing setting processes setting the criterial value K. The setting process may be performed before a comparison determination between Im and Is in the abnormality diagnosis process shown in FIG. 10. For example, the setting process may be performed just before S45 in the flowchart of FIG. 10. When the process in FIG. 11 is performed, the conditions performing the abnormality diagnosis process are different from the above conditions performing the abnormality diagnosis process. As shown in FIG. 11 (a), the abnormality diagnosis is performed regardless of whether or not the engine is in the lean combustion state. As shown in FIG. 11 (b), the abnormality diagnosis is further performed even when the engine is in the fuel cut state. In other words, the abnormality diagnosis process is performed even in a condition other than in the lean combustion state. Similar to the above embodiment, the conditions performing the abnormality diagnosis include the condition that the NOx sensor 10 is active.

As shown in FIG. 11 (a), whether or not the engine is currently in the lean combustion state is determined at S51. When the engine is in the lean combustion state, the microcomputer proceeds to S52. When the engine is in a combustion state other than the lean combustion state, the microcomputer proceeds to S53. The criterial value K at S52 is expressed as "a", and the criterial value K at S53 is expressed as "b". In this case, a is smaller than b. Therefore, the criterial value K in the lean combustion state is smaller than that in a combustion state other than the lean combustion state.

In other words, when the engine 50 is in the lean combustion state, the amount of NOx in the exhaust gas is larger than that of when the engine 50 is in a combustion state other than the lean combustion state. Therefore, in order to ensure that an abnormality diagnosis is performed with the same accuracy regardless of whether the engine is in the lean combustion state or in another combustion state, it is preferable to change the criterial value K depending on the combustion state of the engine. In the modified embodiment, as mentioned above, since the criterial value K in the lean combustion state is smaller than that in a combustion state other than the lean combustion state, the accuracy of the sensor abnormality diagnosis can be improved regardless of whether or not the engine is in the lean combustion state.

As shown in FIG. 11 (b), whether or not a fuel cut (F/C) is being performed is determined at S61. When the fuel cut is being performed, the microcomputer proceeds to S62. When the fuel cut is not being performed, the microcomputer proceeds to S63. The criterial value K at S62 is expressed as "c", and the criterial value K at S63 is expressed as "d". In this case, c is larger than d. Therefore, the criterial value K of when the fuel cut is being performed is larger than that of when fuel cut is not being performed. Then, the comparison determination between Im and Is is performed using the critical value K set as shown in FIG. 11 (a) or FIG. 11 (b).

In other words, when the engine 50 is in the fuel cut state, the amount of the NOx in the exhaust gas is almost zero. Therefore, in order to ensure that an abnormality diagnosis is performed with the same accuracy regardless of whether the fuel cut is being performed or not (a normal operation state), it is preferable to change the criterial value K depending on whether or not the fuel cut is being performed. In the modified embodiment, as mentioned above, since the criterial value K of when fuel cut is being performed is larger than that of when fuel cut is not being performed, the accuracy of the sensor abnormality diagnosis can be improved regardless of whether or not fuel cut is being performed.

In the process in FIG. 11 (b), a process determining whether or not the fuel cut is being performed may be a process determining whether or not the engine 50 is in the combustion state, or may be a process determining whether or not an operation of the engine 50 is just stopped (a warming-up stop state).

The processes shown in FIG. 11 (a) and FIG. 11 (b) may be integrated into one process. In this case, the criterial value K is selectively set in three states including the lean combustion state, a combustion state other than the lean combustion state, and the fuel cut state (a combustion stop state). When the criterial values for the three states are expressed as Ka, Kb, and Kc, Ka is smaller than Kb and Kb is smaller than Kc.

(k) In the above embodiment, when an abnormality diagnosis is performed, the output difference ΔI calculated by subtracting the sensor cell current Is from the monitor cell current Im is used as a parameter of the abnormality diagnosis. Alternatively, for example, the ratio of the monitor cell current Im to the sensor cell current Is (Im/Is) may be used as the parameter of the abnormality diagnosis. The parameter of the abnormality diagnosis may be a relative difference of the monitor cell detected value from the sensor cell detected value.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

The invention claimed is:

1. A gas sensor control device for a gas sensor including a first cell and a second cell each having a solid electrolytic element and a pair of electrodes disposed on the solid electrolytic element, the gas sensor discharging an oxygen in a detected gas introduced into a gas chamber, by using the first cell, and the gas sensor detecting a concentration of a specific component from a gas after the oxygen is discharged, by using the second cell, the gas sensor control device comprising:
- a CPU and a storage memory storing instructions which upon execution by the CPU provides a configuration to at least perform:
  - an oxygen discharge amount change which includes sending an instruction to change a voltage of the first cell to thereby temporarily change an oxygen discharge amount that is an amount of the oxygen that is discharged, by the first cell;
  - a first calculation which calculates an actual discharge amount that is an actual amount of a change of the oxygen discharged when the oxygen discharge amount is changed by the oxygen discharge amount change;
  - a second calculation which calculates an amount of output change which occurs in the second cell as a result of changing the oxygen discharge amount by the oxygen discharge amount change; and
  - a control which performs deterioration diagnosis of the second cell, based on the actual discharge amount as calculated by the first calculation and the amount of output change of the second cell as calculated by the second calculation,
- wherein the control includes a deterioration diagnosis which calculates an output sensitivity value of the second cell based on the actual discharge amount and the amount of the output change of the second cell and performing a deterioration diagnosis of the second cell.

2. The gas sensor control device according to claim 1, wherein:
- the oxygen discharge amount change temporarily decreases the amount of oxygen discharge by the first cell;
- the first calculation calculates an amount of a decrease of an actual oxygen discharge as a result of decreasing the amount of oxygen discharge by the first cell, as the actual discharge amount;
- the second calculation calculates an increase amount of output change of the second cell as a result of decreasing the amount of oxygen discharge by the first cell; and
- the control performs at least either correction of the concentration of the specific component as detected by the second cell or the deterioration diagnosis, based on the amount of the decrease of the actual oxygen discharge as calculated by the first calculation and the amount of output increase in the second cell as calculated by the second calculation.

3. The gas sensor control device according to claim 2, wherein execution of the instructions by the CPU further provides the configuration to at least perform:
- a diagnosis which determines that the concentration of the specific component of the detected gas is below a prescribed value,
- wherein the oxygen discharge amount change temporarily decreases the amount of oxygen discharge by the first cell when the diagnosis determines that the concentration of the specific component is below the prescribed value.

4. The gas sensor control device according to claim 3, wherein:
- the gas sensor is an exhaust gas sensor which takes exhaust gas discharged from an internal combustion engine as an object of detection and detects a concentration of a specific component in the exhaust gas,
- the diagnosis determines that the concentration of the specific component is below a prescribed value when fuel cut is being performed in the internal combustion engine, and
- the oxygen discharge amount change temporarily decreases the amount of oxygen discharge by the first cell when fuel cut is being performed in the internal combustion engine.

5. The gas sensor control device according to claim 4, wherein:
- the gas sensor is a NOx sensor which detects a concentration of NOx in the exhaust gas, and
- the oxygen discharge amount change discharges oxygen equivalent to 2000 to 3000 ppm as the NOx concentration, using the first cell.

6. The gas sensor control device according to claim 1, wherein execution of the instructions by the CPU further provides the configuration to at least perform:
- a setting which, when the oxygen discharge amount is changed by the oxygen discharge amount change, varies the oxygen discharge amount depending on the concentration of the specific component before change of the oxygen discharge amount.

7. The gas sensor control device according to claim 1, wherein the second cell is a sensor cell which detects a concentration of a component other than oxygen as the concentration of the specific component from gas after oxygen discharge by the first cell.

8. The gas sensor control device according to claim 1, wherein the second cell is a monitor cell which detects a concentration of residual oxygen in the gas chamber as the concentration of the specific component, from gas after oxygen discharge by the first cell.

9. The gas sensor control device according to claim 1, wherein the control includes a concentration correction which calculates an output correction value of the second cell based on the actual discharge amount and the amount of the output change of the second cell and performing a correction of the concentration of the specific component as detected by the second cell.

10. A gas sensor control device for a gas sensor including a first cell and a second cell each having a solid electrolytic element and a pair of electrodes disposed on the solid electrolytic element, the gas sensor discharging an oxygen in a detected gas introduced into a gas chamber, by using the first cell, and the gas sensor detecting a concentration of a specific component from a gas after the oxygen is discharged, by using the second cell, the gas sensor control device comprising:
- a CPU and a storage memory storing instructions which upon execution by the CPU provides a configuration to at least perform:
  - an oxygen discharge amount change which includes sending an instruction to change a voltage of the first cell to thereby temporarily change an oxygen discharge amount that is an amount of the oxygen that is discharged, by the first cell;
  - a first calculation which calculates an actual discharge amount that is an actual amount of a change of the oxygen discharged when the oxygen discharge amount is changed by the oxygen discharge amount change;
  - a second calculation which calculates an amount of output change which occurs in the second cell as a result of changing the oxygen discharge amount by the oxygen discharge amount change; and a control which performs at least either correction of the concentration of the specific component as detected by the second cell or deterioration diagnosis of the second cell, based on the actual discharge amount as calculated by the first calculation and the amount of output change of the second cell as calculated by the second calculation; wherein:

the oxygen discharge amount change temporarily decreases the amount of oxygen discharge by the first cell;

the first calculation calculates an amount of a decrease of an actual oxygen discharge as a result of decreasing the amount of oxygen discharge by the first cell, as the actual discharge amount;

the second calculation calculates an increase amount of output change of the second cell as a result of decreasing the amount of oxygen discharge by the first cell; and the control performs at least either the correction of the concentration or the deterioration diagnosis, based on the amount of the decrease of the actual oxygen discharge as calculated by the first calculation and the amount of output increase in the second cell as calculated by the second calculation.

11. A gas sensor control device for a gas sensor including a first cell and a second cell each having a solid electrolytic element and a pair of electrodes disposed on the solid electrolytic element, the gas sensor discharging an oxygen in a detected gas introduced into a gas chamber, by using the first cell, and the gas sensor detecting a concentration of a specific component from a gas after the oxygen is discharged, by using the second cell, the gas sensor control device comprising:

a CPU and a storage memory storing instructions which upon execution by the CPU provides a configuration to at least perform:

an oxygen discharge amount change which includes sending an instruction to change a voltage of the first cell to thereby temporarily change an oxygen discharge amount that is an amount of the oxygen that is discharged, by the first cell;

a first calculation which calculates an actual discharge amount that is an actual amount of a change of the oxygen discharged when the oxygen discharge amount is changed by the oxygen discharge amount change;

a second calculation which calculates an amount of output change which occurs in the second cell as a result of changing the oxygen discharge amount by the oxygen discharge amount change;

a control which performs at least either correction of the concentration of the specific component as detected by the second cell or deterioration diagnosis of the second cell, based on the actual discharge amount as calculated by the first calculation and the amount of output change of the second cell as calculated by the second calculation; and a setting which, when the oxygen discharge amount is changed by the oxygen discharge amount change, varies the oxygen discharge amount depending on the concentration of the specific component before change of the oxygen discharge amount.

* * * * *